United States Patent [19]

Baltes et al.

[11] 4,302,609

[45] Nov. 24, 1981

[54] PROCESS FOR THE MANUFACTURE OF METHYLGLYOXAL

[75] Inventors: Herbert Baltes, Frankfurt am Main; Ernst I. Leupold, Neu-Anspach, both of Fed. Rep. of Germany

[73] Assignee: Hoechst Aktiengesellschaft, Frankfurt am Main, Fed. Rep. of Germany

[21] Appl. No.: 165,693

[22] Filed: Jul. 3, 1980

[30] Foreign Application Priority Data

Jul. 7, 1979 [DE] Fed. Rep. of Germany ....... 2927524

[51] Int. Cl.$^3$ ............... C07C 45/32; C07C 47/127
[52] U.S. Cl. ................................. 568/471; 568/473; 568/474
[58] Field of Search ................ 568/474, 471, 473

[56] References Cited

U.S. PATENT DOCUMENTS

| | | | |
|---|---|---|---|
| 2,051,266 | 8/1936 | McAllister | 568/471 |
| 2,339,282 | 1/1944 | McNamee | 568/471 |
| 2,339,346 | 1/1944 | McNamee | 568/471 |
| 3,948,997 | 4/1976 | Howe et al. | 568/471 |
| 3,991,117 | 11/1976 | Zeidler et al. | 568/471 |

OTHER PUBLICATIONS

Houben–Weyl "Methoden oder organischen Chemie" vol. VII/12 pp. 771 et seq; VII/2 p. 708; vol. VIII/1 p. 235 (1943).
Sander et al. "Ind. Eng. Chem." vol. 46 pp. 414–426 (1954).
Zdrodovskaya et al. "Chem. Abst." vol. 55, 7511c (1961).

*Primary Examiner*—Werren B. Lone
*Attorney, Agent, or Firm*—Curtis, Morris & Safford

[57] ABSTRACT

Methylglyoxal is manufactured continuously by passing glycerol in the gaseous phase over a heterogeneous dehydrogenation catalyst.

7 Claims, No Drawings

PROCESS FOR THE MANUFACTURE OF METHYLGLYOXAL

The invention relates to a process for the manufacture of methylglyoxal by a reaction of glycerol in the gaseous phase catalyzed by a heterogeneous catalyst.

It is known that glycerol can be reacted in two steps to give methylglyoxal by passing over 1,3-dihydroxyacetone (E. P. Zdrodovskaya and S. M. Zhdan-Pushkina, C. A. 55, 7511 c). The dehydrogenation of glycerol to 1,3-dihydroxyacetone (step 1) is carried out with the aid of microorganisms (Acetobacter melanogenum) (see also: Houben-Weyl, Methoden der organischen Chemie, Vol. VII/12, a, page 771 et seq.). The 1,3-dihydroxyacetone can subsequently be rearranged (step 2) in the presence of an acidic to yield methylglyoxal (DE-PS No. 1,914,037).

Such a two-step reaction considerably impairs a continuous process; the bacterial dehydrogenation (step 1) furthermore requies very dilute aqueous glycerol solutions and therefore great reaction volumes. These disadvantages and long reaction periods as well as complicated working-up steps considerably impair the profitability of these two-step processes.

Methylglyoxal, in general, is manufactured industrially by catalytic dehydrogenation of propylene glycol. By-products or secondary products formed in this reaction are formaldehyde, carbon oxides, propionaldehyde, hydroxypropanone and stable acetals or ketals or high boiling point, which are formed by the reaction of the said aldehydes or ketones with unreacted propylene glycol (DE-PS No. 1,914,038; US-PA No. 2,339,346; US-PS No. 2,051,266).

An object of the present invention resides in a continuous process for the manufacture of methylglyoxal overcoming previously known problems.

The subject matter of the present invention relates to a process for the continuous manufacture of methylglyoxal, which comprises passing glycerol over a heterogeneous dehydrogenation catalyst in the gaseous phase.

According to Houben-Weyl, methoden oder organischen Chemie, Vol. VII/2 a, page 708 and Vol. VII/1, page 235 et seq., glycerol is easily rearranged by heterogeneous catalysts, to yield acrolein while splitting off water. Therefore, it was unexpected that glycerol could be reacted in the gaseous phase to yield methylglyoxal in a one-step process in the presence of a heterogeneous catalyst.

The gaseous glycerol is conducted over the catalyst alone or—preferably—together with steam and/or a carrier gas. Carrier gases can be, for example, nitrogen and noble gases, but also lower saturated hydrocarbons, such as methane, ethane or propane.

It has proven advantageous with admix to the gaseous glycerol oxygen or an oxygen-containing gas, for example air. If air is employed, it also fulfils the function of the carrier gas.

In accordance with the process of the invention the following amounts of additional substances can be used per mol of glycerol:

water: 0–15 mols, preferably 0.1–8 mols
oxygen or oxygen-containing gas: 0–8 mols, preferably 0.5–5 mols,
carrier gas: 0–80 mols, preferably 10–80 mols, esspecially 40–60 mols.

Satisfactory results are also obtained beyond these limits.

As dehydrogenation catalyst there is used in general at least one of the following elements either in metallic form or as a compound: vanadium, molybdenum, tungsten, copper, silver, tin, lead, antimony, bismuth, iron.

Vanadium, molybdenum, copper, silver, tin and/or antimony are preferably used. Especially preferred are catalysts which contain vanadium and/or molybdenum, particularly if they contain additionally tin and/or silver.

The afore-mentioned elements are introduced into the reaction zone either in metallic form or in form of their compounds, for example as oxides, nitrates, acetates, acetyl-acetonates, oxalates, citrates or halides.

Other dehydrogenation catalysts, however also exhibit a catalytic action, especially if they contain at least one element able of forming basic or amphoteric oxides.

It has proved advantageous to pass an oxidizing gas, especially oxygen or air, or a reducing gas, particularly hydrogen or hydrogen diluted with an inert gas, over the catalyst, at temperature of from 100° to 800° C., especially from 300° to 600° C., to activate the catalyst, before introducing glycerol into the reaction zone.

The catalytically active elements are preferably applied onto carrier materials. Suitable carriers are, first of all, silicates, aluminum oxides, aluminum silicates, pumice or coals. Silicates, aluminum oxides or aluminum silicates are preferably used. Aluminum silicates with a BET surface of less than 20 m²/g are especially advantageous.

The total amount of catalytically active elements can vary within a wide range. In general, it ranges between 0.01 and 50 percent by weight, preferably between 0.1 and 20 percent by weight, relative to the total mass of the carrier catalyst. The catalytically active components are expediently applied onto the carrier in the form of a solution; subsequently, the solvent is evaporated and the catalyst is dried. The solvents generally used are water, hydrochloric acid, nitric acid, aqueous alkali hydroxides or aqueous ammonia solutions, preferably water.

The active components, however, can also be used without a carrier.

The process according to the invention is carried out, in general, at temperatures between 100° and 600° C., preferably at temperatures between 200° and 450° C.

The residence time is preferably between 0.1 and 10 seconds, especially, however, between 0.1 and 1 second. But even beyond these limits satisfactory results can be obtained.

The process according to the invention is preferably carried out at normal pressure, but reduced or elevated pressures can also be used (0.01 to 100 bars).

In particular, the glycerol or a mixture of glycerol and water is introduced by a metering device into an evaporation zone and the evolved gas is then passed through a reaction tube which is externally heated charged with the catalyst. Mixing with the carrier gas and/or the oxygen or the oxygen-containing gas optionally takes place in the evaporation zone; it has proved advantageous to heat these gases to the reaction temperature before mixing.

After leaving the reactor, the reaction products are cooled to separate the condensible portions. Methylglyoxal can be isolated from the condensate according to the usual methods, for example according to DE-PS No. 1,914,038 by rapid distillation or according to US-PS No. 2,866,823 as dimethylacetal.

When a mixture of glycerol and water is used, the condensate is an aqueous solution which can directly be used for many applications, for example for the manufacture of acetals of methylglyoxal (US-PS No. 2,421,559).

Methylglyoxal and the acetals of methylglyoxal, due to their high reactivity, are suitable as intermediates for the manufacture of many chemical compounds, for example highly effective insecticides of the allethrin type (H.-J. Sanders and A. W. Taff, Ind. Eng. Chem. 46, 414–426 (1954).

The following examples illustrate the invention.

EXAMPLE 1

12 ml/h of a 50% aqueous glycerol solution are introduced into a glass reactor in vertical position of 150 mm length and of 20 mm diameter by the aid of an injection plunger by passing through an evaporation zone. At the same time, 56 Nl/h of nitrogen and 0.8 Nl/h of oxygen, which both have been heated previously to 350° C., are introduced into the evaporation zone.

The reactor is also externally heated to 350° C. and is charged with 15 mol of an aluminum silicate catalyst containing 4.6% by weight of vanadium and 5.4 % by weight of tin and which has a BET surface of about 1 $m^2/g$.

For the manufacture of the catalyst, there are dissolved 8.2 g of tin-II-chloride ($SnCl_2 = 2H_2O$) and 8.5 g ammonium vanadate ($NH_4VO_3$) in 50 ml of concentrated hydrochloric acid, 72 g of the catalyst carrier is impregnated with this solution and the solvent is evaporated on a steam bath. Subsequently, the catalyst is dried at 110° C. and then heated to 400° C. in the reactor in a gas flow of 56 Nl/h of nitrogen and 3 Nl/h of oxygen, for three hours.

The temperature within the reactor is measured by the aid of a thermoelement. The reaction products are condensated in a cooling trap at −70° C.

After a starting period of 1 H for adjusting constant conditions of operation, the actual catalyst test is carried out for a period of 2 hours. The condensate is analyzed by liquid chromatography.

After a 2 hours' test there are obtained 60.3 mmols of methylglyoxal, corresponding to a selectivity of 76%. The yield of acrolein, relative to the glycerol used, is less than 0.5%.

EXAMPLE 2

Analogously to Example 1, there are introduced into the apparatus described in Example 1 6 ml/h glycerol, 3.7 Nl/h of oxygen and 56 Nl/h of nitrogen. The reactor contains 15 ml of an aluminum silicate catalyst containing 5.0 percent by weight of silver and 5.0 percent by weight of vanadium on a carrier, as in Example 1, and which is heated to 350° C.

The result of a two hours' test are 98.6 mmols of methylglyoxal, corresponding to a selectivity of 81%.

EXAMPLE 3

Analogously to Example 1, there are introduced into the apparatus described in Example 1 12 ml/h of a 50% aqueous glycerol solution, 1.6 Nl/h of oxygen and 56 Nl/h of nitrogen. The reactor contains 15 ml of an aluminum silicate catalyst, which contains 4.0% by weight of vanadium, 4.0% by weight of silver, 1.0% by weight of copper and 1.0% by weight of iron on a carrier as in Example 1, and is heated to 350° C.

After a two hours' test there are obtained 80.8 mmols of methylglyoxal, corresponding to a selectivity of 82%.

EXAMPLE 4

Analogously to Example 1, there are introduced into the apparatus described in Example 1 12 ml/h of a 50% aqueous glycerol solution and 20 Nl/h of air. The reactor contains 15 ml of an aluminum silicate catalyst, which contains 4.0% by weight of vanadium, 5.0% by weight of silver, 0.5% by weight of molybdenum and 0.5 % by weight of bismuth on a carrier as in Example 1, and which is heated to 250° C.

As a result of a two hours' test there are obtained 70.7 mmols of methylglyoxal, corresponding to a selectivity of 69%.

EXAMPLE 5

Analogously to Example 1, there are introduced into the apparatus described in Example 1 24 ml/h of a 50% aqueous glycerol solution, 3.2 Nl/h of oxygen and 56 Nl/h of nitrogen. The reactor contains 15 ml of an aluminum silicate catalyst which contains 2.8% by weight of vanadium, 6.8% by weight of antimony, 0.3% by weight of lead and 0.1% by weight of tungsten on a carrier as in Example 1 and which is heated to 450° C.

As result of a two hours' test there are obtained 129.2 mmols of methylglyoxal, corresponding to a selectivity of 55%.

What is claimed is:

1. A process for the continuous manufacture of methylglyoxal which comprises passing glycerol, in the gaseous phase, over a heterogeneous dehydrogenation catalyst containing a catalytically effective amount of at least one element selected from the group consisting of vanadium, molybdenum, tungsten, cooper, silver, tin, lead, antimony, bismuth and iron said process being conducted at a temperature in the range of 100° to 600° C. and a pressure in the range of 0.01 to 100 bars in the presence of oxygen or an oxygen-containing gas.

2. The process of claim 1 wherein the catalyst contains at least one element selected from the group consisting of vanadium, molybdenum, copper, silver, tin and antimony.

3. The process of claim 1 wherein the catalyst contains vanadium or molybdenum, or both.

4. The process of claim 3 wherein the catalyst additionally contains tin or silver, or both.

5. The process of any one of claims 12 to 14 wherein the catalyst is applied onto a suitable carrier having a BET surface of less than 20 $m^2/g$.

6. The process of claim 1 wherein glycerol is evaporated together with water.

7. The process of claim 1 wherein said process is conducted at a temperature in the range of 250° C. to 450° C.

* * * * *